United States Patent
Eickelmann et al.

(10) Patent No.: US 7,371,732 B2
(45) Date of Patent: May 13, 2008

(54) GLUCOPYRANOSYLOXY-SUBSTITUTED AROMATIC COMPOUNDS, MEDICAMENTS CONTAINING SUCH COMPOUNDS, THEIR USE AND PROCESS FOR THEIR MANUFACTURE

(75) Inventors: Peter Eickelmann, Mittelbiberach (DE); Frank Himmelsbach, Mittelbiberach (DE); Edward Leon Barsoumian, Toyonaka (JP)

(73) Assignee: Boehringer Ingelheim International GmbH, Ingelheim (DE)

( * ) Notice: Subject to any disclaimer, the term of this patent is extended or adjusted under 35 U.S.C. 154(b) by 293 days.

(21) Appl. No.: 11/018,870

(22) Filed: Dec. 21, 2004

(65) Prior Publication Data

US 2005/0187168 A1    Aug. 25, 2005

Related U.S. Application Data

(60) Provisional application No. 60/538,560, filed on Jan. 23, 2004.

(30) Foreign Application Priority Data

Dec. 22, 2003   (DE)   ................ 103 61 133

(51) Int. Cl.
  *A61K 31/70*    (2006.01)
  *A61K 31/7004*  (2006.01)
  *C07H 15/203*   (2006.01)
(52) U.S. Cl. .................. 514/25; 536/4.1
(58) Field of Classification Search .......... 514/25; 536/4.1, 17.2
See application file for complete search history.

(56) References Cited

U.S. PATENT DOCUMENTS

| | | | |
|---|---|---|---|
| 6,414,126 B1 * | 7/2002 | Ellsworth et al. | 536/17.2 |
| 6,627,611 B2 * | 9/2003 | Tomiyama et al. | 514/23 |
| 2005/0059614 A1 * | 3/2005 | Fujikura et al. | 514/25 |
| 2005/0080022 A1 * | 4/2005 | Fujikura et al. | 514/25 |
| 2005/0113315 A1 * | 5/2005 | Fujikura et al. | 514/25 |

FOREIGN PATENT DOCUMENTS

WO   WO 01/74834 A   10/2001

OTHER PUBLICATIONS

Adachi et al., "T-1095, a Renal Na+-Glucose Transporter Inhibitor, Improves Hyperglycemia in Streptozotocin-Induced Diabetic Rats" Metabolism (2000) vol. 49, No. 8, pp. 990-995.*

* cited by examiner

*Primary Examiner*—Shaojia Anna Jiang
*Assistant Examiner*—Eric S Olson
(74) *Attorney, Agent, or Firm*—Michael Morris; David Dow; Mary-Ellen M. Devlin

(57) ABSTRACT

The present invention relates to glucopyranosyloxy-substituted aromatic groups of general formula

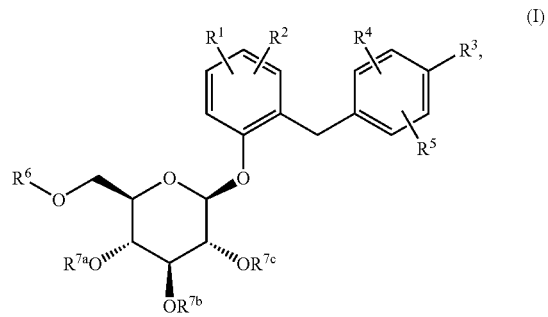

(I)

wherein
$R^1$ to $R^6$ and $R^{7a}$, $R^{7b}$, $R^{7c}$ are defined as in claim 1, the tautomers, the stereoisomers, the mixtures thereof and the salts thereof, particularly the physiologically acceptable salts thereof with inorganic or organic acids, which have valuable pharmacological properties, particularly an inhibitory effect on the sodium-dependent glucose cotransporter SGLT2, the use thereof for the treatment of diseases, particularly metabolic disorders such as diabetes, and the preparation thereof.

28 Claims, No Drawings

GLUCOPYRANOSYLOXY-SUBSTITUTED AROMATIC COMPOUNDS, MEDICAMENTS CONTAINING SUCH COMPOUNDS, THEIR USE AND PROCESS FOR THEIR MANUFACTURE

RELATED APPLICATIONS

This application claims benefit to DE 10361133.9 filed Dec. 22, 2003 and U.S. provisional application No. 60/583,560 filed Jan. 23, 2004 and the contents of each is incorporated herein.

The present invention relates to glucopyranosyloxy-substituted aromatic groups of general formula I

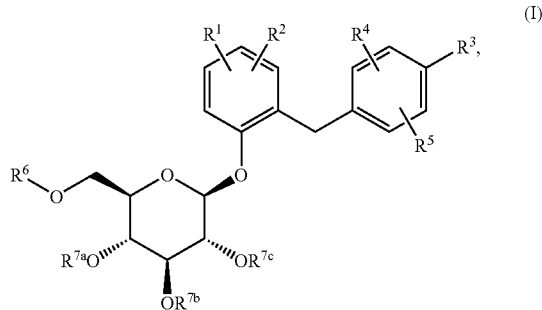

wherein the groups $R^1$ to $R^6$ and $R^{7a}$, $R^{7b}$ and $R^{7c}$ are as defined hereinafter, including the tautomers, the stereoisomers, the mixtures thereof and the salts thereof. The invention also relates to pharmaceutical compositions containing a compound of formula I according to the invention as well as the use of a compound according to the invention for preparing a pharmaceutical composition for the treatment of metabolic disorders. Processes for preparing a pharmaceutical composition and a compound according to the invention are also the subject of this invention.

In the literature, compounds which have an inhibitory effect on the sodium-dependent glucose cotransporter SGLT2 are proposed for the treatment of diseases, particularly diabetes.

Glucopyranosyloxy-substituted aromatic groups and the preparation thereof and their possible activity as SGLT2 inhibitors are known from published International applications WO 01/68660, WO 01/74834, WO 02/28872, WO 02/44192, WO 02/64606, WO 03/11880 as well as WO 03/80635.

AIM OF THE INVENTION

The aim of the present invention is to find new glucopyranosyloxy-substituted aromatic groups, particularly those which are active with regard to the sodium-dependent glucose cotransporter SGLT, particularly SGLT2. A further aim of the present invention is to discover glucopyranosyloxy-substituted aromatic groups which have an enhanced inhibitory effect on the sodium-dependent glucose cotransporter SGLT2 in vitro and/or in vivo compared with known, structurally similar compounds and/or have better pharmacological or pharmacokinetic properties.

A further aim of the present invention is to provide new pharmaceutical compositions which are suitable for the prevention and/or treatment of metabolic disorders, particularly diabetes.

The invention also sets out to provide a process for preparing the compounds according to the invention.

Other aims of the present invention will become apparent to the skilled man directly from the foregoing and following remarks.

OBJECT OF THE INVENTION

In a first aspect the present invention relates to glucopyranosyloxy-substituted aromatic groups of general formula I

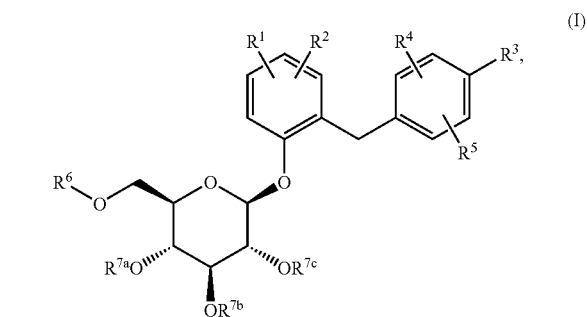

wherein
$R^1$ denotes $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy or tetrahydropyranyl-$C_{1-3}$-alkyloxy, or,
if $R^3$
is selected from the group consisting of $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy and tetrahydropyranyl-$C_{1-3}$-alkyloxy,
then $R^1$ may additionally also represent hydrogen, fluorine, chlorine, bromine, iodine, $C_{1-4}$-alkyl, a methyl group substituted by 1 to 3 fluorine atoms, an ethyl group substituted by 1 to 5 fluorine atoms, $C_{1-4}$-alkoxy, a methoxy group substituted by 1 to 3 fluorine atoms, an ethoxy group substituted by 1 to 5 fluorine atoms, a $C_{1-4}$-alkyl group substituted by a hydroxy or $C_{1-3}$-alkoxy group, a $C_{2-4}$-alkoxy group substituted by a hydroxy or $C_{1-3}$-alkoxy group, $C_{2-6}$-alkenyl, $C_{3-6}$-cycloalkyl, $C_{3-6}$-cycloalkyl-$C_{1-3}$-alkyl, $C_{3-6}$-cycloalkoxy, $C_{3-6}$-cycloalkyl-$C_{1-3}$-alkoxy, hydroxy, amino or cyano, and
$R^2$ denotes hydrogen, fluorine, chlorine, methyl, methyl or methoxy substituted by 1 to 3 fluorine atoms, and
$R^3$ denotes $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy or tetrahydropyranyl-$C_{1-3}$-alkyloxy, or,
if $R^1$ is selected from the group consisting of
$C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy and tetrahydropyranyl-$C_{1-3}$-alkyloxy,
then $R^3$ may additionally also represent hydrogen, fluorine, chlorine, bromine, iodine, $C_{1-6}$-alkyl, $C_{2-6}$-alkenyl, $C_{3-6}$-cycloalkyl, $C_{3-6}$-cycloalkylidenemethyl, $C_{1-6}$-alkoxy, $C_{3-6}$-cycloalkyl-oxy, $C_{3-6}$-cycloalkyl-$C_{1-3}$-alkoxy, aryl, aryl-$C_{1-3}$-alkyl, heteroaryl, heteroaryl-$C_{1-3}$-alkyl, aryloxy, aryl-$C_{1-3}$-alkyl-oxy, a methyl or methoxy group substituted by 1 to 3 fluorine atoms, a $C_{2-4}$-alkyl or $C_{2-4}$-alkoxy group substituted by 1 to 5 fluorine atoms, a $C_{1-4}$-alkyl group substituted by a cyano group, a $C_{1-4}$-alkyl group substituted by a hydroxy or $C_{1-3}$-alkyloxy group, cyano, carboxy, $C_{1-3}$-alkoxycarbonyl, aminocarbonyl, ($C_{1-3}$-alkylamino)carbonyl, di-($C_{1-3}$-alkyl)aminocarbonyl, pyrrolidin-1-ylcarbonyl, piperidin-1-ylcarbonyl, morpholin-4-ylcarbonyl, piperazin-1-yl-carbonyl, 4-($C_{1-3}$-alkyl)-piperazin-1-ylcarbonyl, nitro, amino, $C_{1-3}$-alkylamino, di-($C_{1-3}$-alkyl)amino, ($C_{1-4}$-alkyl)carbonylamino, $C_{1-4}$-alkylsulphonylamino, arylsulphonylamino, aryl-$C_{1-3}$-alkylsulphonylamino, $C_{1-4}$-alkylsulphanyl, $C_{1-4}$-alkylsulphinyl, $C_{1-4}$-alkylsulphonyl, arylsulphenyl, arylsulphinyl or arylsulphonyl, $R^4$ and $R^5$, which may be identical or different, represent hydrogen, fluorine, chlorine, bromine, $C_{1-3}$-alkyl, $C_{1-3}$-alkoxy, methyl or methoxy substituted by 1 to 3 fluorine atoms, and $R^6$, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, while the aryl groups mentioned in the definition of the above groups are meant to indicate phenyl or naphthyl groups which may be mono- or disubstituted independently of one another by $R_h$, while the substituents may be identical or different and $R_h$ denotes a fluorine, chlorine, bromine, iodine, $C_{1-3}$-alkyl, difluoromethyl, trifluoromethyl, $C_{1-3}$-alkoxy, difluoromethoxy, trifluoromethoxy or cyano, the heteroaryl groups mentioned in the definition of the above-mentioned groups are meant to indicate a pyrrolyl, furanyl, thienyl, imidazolyl, pyridyl, indolyl, benzofuranyl, benzothiophenyl, quinolinyl or isoquinolinyl group, or a pyrrolyl, furanyl, thienyl, imidazolyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted by $R_h$, while the substituents may be identical or different and $R_h$ is as hereinbefore defined, while, unless otherwise stated, the above-mentioned alkyl groups may be straight-chain or branched, the tautomers, the stereoisomers, the mixtures thereof and the salts thereof.

The compounds of general formula I according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

Therefore, the invention also relates to the use of the compounds according to the invention, including the physiologically acceptable salts, as pharmaceutical compositions.

This invention also relates to pharmaceutical compositions, containing at least one compound according to the invention or a physiologically acceptable salt according to the invention, optionally together with one or more inert carriers and/or diluents.

A further subject of this invention is the use of at least one compound according to the invention or a physiologically acceptable salt of such a compound for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention or one of the physiologically acceptable salts thereof for preparing a pharmaceutical composition which is suitable for the treatment of metabolic disorders.

This invention also relates to the use of at least one compound according to the invention or one of the physiologically acceptable salts thereof for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention is incorporated in one or more inert carriers and/or diluents by a non-chemical method.

The present invention also relates to a process for preparing the compounds of general formula I according to the invention, characterised in that a) in order to prepare compounds of general formula I wherein $R^6$, $R^{7a}$, $R^{7b}$ and $R^{7c}$ are as hereinbefore defined, but do not represent hydrogen, a compound of general formula

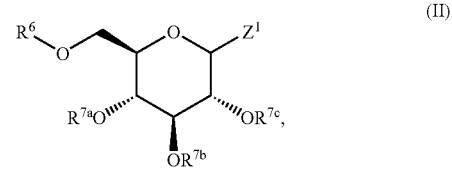

(II)

wherein $R^6$ and $R^{7a}$, $R^{7b}$, $R^{7c}$ are as hereinbefore defined, but do not represent hydrogen, and $Z^1$ denotes a leaving group, is reacted with a compound of general formula

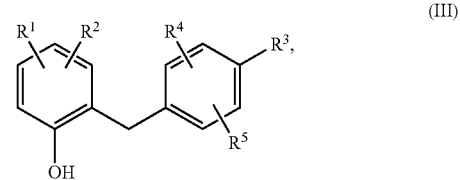

(III)

wherein $R^1$ to $R^5$ have the meanings given hereinbefore, or b) in order to prepare compounds of general formula I wherein $R^6$, $R^{7a}$, $R^{7b}$ and $R^{7c}$ represent hydrogen, a compound of general formula I wherein $R^6$ and $R^{7a}$, $R^{7b}$, $R^{7c}$ are as hereinbefore defined, but do not represent hydrogen, is hydrolysed, and after step b) has been carried out, if desired a compound of general formula I thus obtained wherein $R^6$ denotes a hydrogen atom is converted by acylation into a corresponding acyl compound of general formula I, and/or
if necessary a protecting group used during the reactions described above is cleaved again and/or
if desired a compound of general formula I thus obtained is separated into its stereoisomers and/or
a compound of general formula I thus obtained is converted into the salts thereof, particularly for pharmaceutical use into the physiologically acceptable salts thereof.

DETAILED DESCRIPTION OF THE INVENTION

Unless otherwise stated the groups, residues and substituents, particularly $R^1$ to $R^6$ and $R^{7a}$, $R^{7b}$, $R^{7c}$, are defined as above and hereinafter.

If residues, substituents or groups occur several times in a compound, they may have the same or different meanings.

The term aryl used above and hereinafter, for example in the groups $R^3$, $R^6$, $R^{7a}$, $R^{7b}$, $R^{7c}$ and $R^{7d}$ preferably denotes phenyl. According to the general definition and unless otherwise stated, the aryl group, particularly the phenyl group, may be mono- or disubstituted by identical or different groups $R_h$.

The term heteroaryl used above and hereinafter, for example in the groups $R^3$ preferably denotes pyridinyl, pyrimidinyl, pyridazinyl, pyrazinyl, triazinyl, imidazolyl, pyrazolyl, triazolyl, tetrazolyl, oxazolyl, oxadiazolyl, thiazolyl or thiadiazolyl. According to the general definition and unless otherwise stated, the heteroaryl group may be mono- or disubstituted by identical or different groups $R_h$.

Compounds according to the invention, in a first embodiment of this invention, may be described by general formula I, wherein $R^1$ denotes $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy or tetrahydropyranyl-$C_{1-3}$-alkyloxy and the other groups $R^2$ to $R^6$ as well as $R^{7a}$, $R^{7b}$, $R^{7c}$ are as hereinbefore defined, including the tautomers, the stereoisomers, the mixtures thereof and the salts thereof.

Preferred meanings of the group $R^1$ according to this embodiment are ethynyl, 2-propyn-1-yl, 2-butyn-1-yl, tetrahydrofuran-3-yloxy, tetrahydropyran-3-yloxy, tetrahydropyran-4-yloxy, tetrahydrofuranylmethyloxy and tetrahydropyranylmethyloxy. Most particularly preferred meanings are ethynyl, tetrahydrofuran-3-yloxy and tetrahydropyran-4-yloxy, particularly ethynyl.

Preferred meanings of the group $R^3$ according to this embodiment are hydrogen, fluorine, chlorine, methyl, ethyl, isopropyl, tert.-butyl, 2-cyano-2-propyl, difluoromethyl, trifluoromethyl, cyclopropyl, cyclobutyl, cyclopentyl, methoxy, ethoxy, isopropoxy, difluoromethoxy, trifluoromethoxy, 1,1,2,2-tetrafluoroethoxy, cylopropyloxy, cyclobutyloxy, cyclopentyloxy, methylsulphanyl, 2-methyl-1-propen-1-yl, cyclopropylidenemethyl, ethynyl, tetrahydrofuran-3-yloxy, tetrahydropyran-3-yloxy, tetrahydropyran-4-yloxy, tetrahydrofuranylmethyloxy, tetrahydropyranylmethyloxy, phenyl, fluorophenyl, pyridinyl, pyrimidinyl, pyridazinyl, pyrazinyl, imidazolyl, pyrazolyl, triazolyl, tetrazolyl, oxazolyl, oxadiazolyl, thiazolyl or thiadiazolyl. Particularly preferred meanings are ethynyl, tetrahydrofuran-3-yloxy, methyl, ethyl, methoxy, ethoxy, difluoromethoxy, trifluoromethoxy, particularly ethynyl, tetrahydrofuran-3-yloxy and methoxy.

Preferred meanings of the group $R^4$ according to this embodiment are hydrogen and fluorine, particularly hydrogen.

Compounds according to the invention in a second embodiment of this invention may be described by general formula I, wherein $R^1$ denotes hydrogen, fluorine, chlorine, bromine, iodine, $C_{1-4}$-alkyl, methyl substituted by 1 to 3 fluorine atoms, ethyl substituted by 1 to 5 fluorine atoms, $C_{1-4}$-alkoxy, methoxy substituted by 1 to 3 fluorine atoms, ethoxy substituted by 1 to 5 fluorine atoms, $C_{1-4}$-alkyl substituted by a hydroxy or $C_{1-3}$-alkoxy group, $C_{2-4}$-alkoxy substituted by a hydroxy or $C_{1-3}$-alkoxy group, $C_{2-6}$-alkenyl, $C_{3-6}$-cycloalkyl, $C_{3-6}$-cycloalkyl-$C_{1-3}$-alkyl, $C_{3-6}$-cycloalkoxy, $C_{3-6}$-cycloalkyl-$C_{1-3}$-alkoxy, hydroxy, amino or cyano, and may also represent $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy or tetrahydropyranyl-$C_{1-3}$-alkyloxy, and $R^3$ is selected from a group consisting of $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy and tetrahydropyranyl-$C_{1-3}$-alkyloxy, and the other groups, particularly $R^2$ and $R^4$ to $R^6$ as well as $R^{7a}$, $R^{7b}$, $R^{7c}$ have the meanings given hereinbefore, including the tautomers, the stereoisomers, the mixtures thereof and the salts thereof.

According to this embodiment preferred meanings of the group $R^1$ are hydrogen, fluorine, chlorine, methyl, difluoromethyl, trifluoromethyl, methoxy, difluoromethoxy, trifluoromethoxy or cyano, particularly preferably hydrogen, fluorine, methyl or cyano, most particularly preferably hydrogen.

According to this embodiment preferred meanings of the group $R^3$ are ethynyl and tetrahydrofuran-3-yloxy.

According to this second embodiment preferred meanings of the group $R^4$ are hydrogen and fluorine, particularly hydrogen.

The following remarks refer to the compounds of formula I, particularly the first and second embodiments mentioned above.

Preferred compounds according to the present invention, particularly according to the first and second embodiments, can be represented by the following formulae (Ia), (Ib), (Ic) and (Id), particularly (Ia), (Ib) and (Ic):

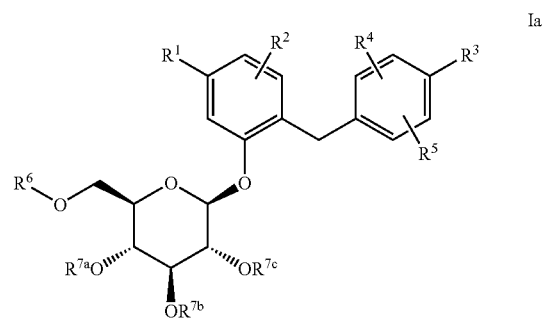

Ia

-continued

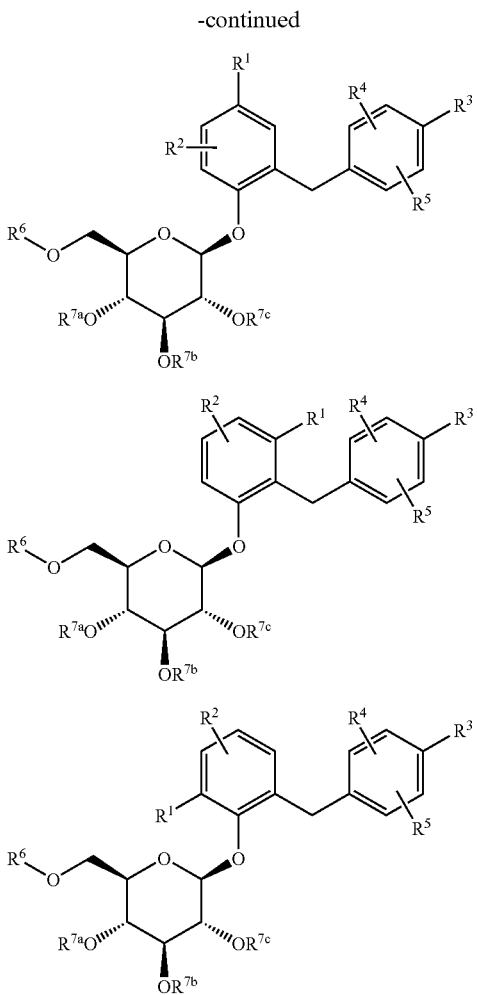

According to an alternative to the embodiments described above, other preferred compounds are those wherein the phenyl group which carries the substituents $R^3$ has at least one other substituent $R^4$ and/or $R^5$ which is not hydrogen. According to this alternative, particularly preferred compounds are those which have a substituent $R^4$ which is fluorine.

The phenyl group which carries the substituent $R^3$ is preferably at most monofluorinated.

Preferred meanings of the group $R^5$ are hydrogen and fluorine, particularly hydrogen.

Preferred meanings of the group $R^2$ according to the invention are hydrogen, fluorine and methyl, particularly hydrogen and methyl.

The group $R^6$ according to the invention preferably denotes hydrogen, $(C_{1-8}$-alkyl)oxycarbonyl or $C_{1-8}$-alkylcarbonyl, particularly hydrogen or $(C_{1-6}$-alkyl)oxycarbonyl, particularly preferably hydrogen, methoxycarbonyl or ethoxycarbonyl, most particularly preferably hydrogen or methoxycarbonyl.

The substituents $R^{7a}$, $R^{7b}$, $R^{7c}$ independently of one another preferably represent hydrogen, $(C_{1-8}$-alkyl)oxycarbonyl, $(C_{1-18}$-alkyl)carbonyl, benzoyl, particularly hydrogen or $(C_{1-6}$-alkyl)oxycarbonyl, $(C_{1-8}$-alkyl)carbonyl, particularly preferably hydrogen, methoxycarbonyl, ethoxycarbonyl, methylcarbonyl or ethylcarbonyl. Most particularly preferably $R^{7a}$, $R^{7b}$ and $R^{7c}$ represent hydrogen.

The compounds of formula I wherein $R^6$, $R^{7a}$, $R^{7b}$ and $R^{7c}$ have a meaning according to the invention other than hydrogen, for example $C_{1-8}$-alkylcarbonyl, are preferably suitable as intermediate products in the synthesis of compounds of formula I wherein $R^{7a}$, $R^{7b}$ and $R^{7c}$ represent hydrogen.

Particularly preferred compounds of general formula I are selected from among:

(a) 1-(β-D-glucopyranosyloxy)-2-[4-((R)-tetrahydrofuran-3-yloxy)benzyl]-benzene, (b) 1-(β-D-glucopyranosyloxy)-2-(4-ethynyl benzyl)-benzene, and the derivatives thereof, wherein $R^6$ has a meaning according to the invention other than hydrogen, and in particular $R^6$ denotes ethoxycarbonyl or methoxycarbonyl, including the stereoisomers and the mixtures thereof.

Some terms used above and hereinafter to describe the compounds according to the invention will now be defined more closely.

The term halogen denotes an atom selected from the group consisting of F, Cl, Br and I, particularly F, Cl and Br.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkynyl, wherein n has a value of 3 to 6, denotes a branched or unbranched hydrocarbon group with 2 to n C atoms and a C≡C double bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl etc.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{3-n}$-cycloalkylcarbonyl denotes a $C_{3-n}$-cycloalkyl-C(=O) group wherein $C_{3-n}$-cycloalkyl is as hereinbefore defined.

The style used above and hereinafter, in which a bond of a substituent in a phenyl group is shown towards the centre of the phenyl ring, denotes, unless otherwise stated, that this substituent may be bound to any free position of the phenyl ring bearing an H atom.

The compounds according to the invention may be obtained using methods of synthesis known in principle. Preferably the compounds are obtained by the following methods according to the invention which are described in more detail hereinafter.

a) In order to prepare compounds of general formula I wherein $R^6$, $R^{7a}$, $R^{7b}$, $R^{7c}$ are as hereinbefore defined, but do not denote a hydrogen atom:
reacting a compound of general formula

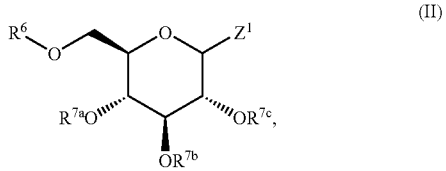

(II)

wherein
$R^6$ and $R^{7a}$, $R^{7b}$, $R^{7c}$ are as hereinbefore defined, but do not represent hydrogen, and $Z^1$ denotes a leaving group such as for example a halogen atom, e.g. a fluorine, chlorine or bromine atom, or an acyloxy group, e.g. an acetyloxy or trichloroacetimidoyloxy group, with a compound of general formula

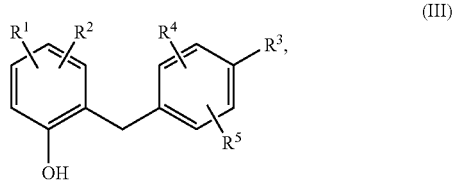

(III)

wherein
$R^1$ to $R^5$ have the meanings specified.

The reaction is conveniently carried out in a solvent, such as for example methylene chloride, chloroform, acetonitrile, toluene, tetrahydrofuran, dioxane, dimethylformamide, dimethylsulphoxide or N-methylpyrrolidinone, optionally in the presence of a base, such as for example potassium carbonate, caesium carbonate, sodium hydride or potassium-tert.-butoxide, or a silver compound such as silver (I) oxide, silver (I) carbonate or silver (I) trifluoroacetate or a catalyst such as for example boron trifluoride etherate at temperatures between −60° C. and 120° C. The reaction may also be carried out for example in a phase transfer system such as sodium hydroxide solution/methylene chloride/benzyl-triethylammonium bromide, while other protective groups such as the trimethylsilyl group on an ethynyl group may be cleaved at the same time.

b) In order to prepare compounds of general formula I wherein $R^6$, $R^{7a}$, $R^{7b}$ and $R^{7c}$ denote hydrogen:
reacting a compound of general formula I wherein
$R^6$, $R^{7a}$, $R^{7b}$ and $R^{7c}$ are as hereinbefore defined, but do not represent hydrogen, with water or a lower alcohol such as methanol or ethanol.

The reaction is conveniently carried out in water, a lower alcohol such as methanol or ethanol or an aqueous solvent mixture such as methanol/tetrahydrofuran, in the presence of a base, such as for example lithium hydroxide, sodium hydroxide, potassium carbonate or sodium methoxide at temperatures between −20° C. and 60° C. In this reaction other protective groups such as the trimethylsilyl group on an ethynyl group may be cleaved at the same time.

If according to the invention a compound of general formula I is obtained wherein $R^6$ denotes a hydrogen atom, this may be converted by acylation, for example by acylation in the presence of a base such as pyridine, collidine, triethylamine or N-ethyl-diisopropylamine, into a compound wherein $R^6$ denotes a ($C_{1-18}$-alkyl)carbonyl group, a ($C_{1-18}$-alkyl)oxycarbonyl group, an arylcarbonyl group or an aryl-($C_{1-3}$-alkyl)-carbonyl group. Suitable acylating agents may be, in particular, the corresponding activated acyl derivatives such as acid chlorides or anhydrides.

In the reactions described hereinbefore, any reactive groups present such as ethynyl, hydroxy, amino, alkylamino or imino groups may be protected during the reaction by conventional protecting groups which are cleaved again after the reaction.

For example, a protecting group for an ethynyl group may be the trimethylsilyl group.

For example, a protecting group for a hydroxy group may be a trimethylsilyl, acetyl, trityl, benzyl or tetrahydropyranyl group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide.

However, a benzyl, methoxybenzyl or benzyloxycarbonyl group is advantageously cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran or methanol at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds of general formulae II to V used as starting materials are partly known from the literature or may be obtained by methods known from the literature (see Examples I to VI), optionally with the additional inclusion of protecting groups.

The compounds according to the invention may advantageously also be obtained by the methods described in the following examples, which may also be combined with methods known to the skilled man from the literature, for example, particularly the methods described in WO 01/68660, WO 01/74834, WO 02/28872, WO 02/44192, WO 02/64606, WO 03/11880 and WO 03/80635.

As already mentioned, the compounds of general formula I according to the invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No.NM_003041) (CHO-hSGLT2 or HEK-hSGLT2). These cell lines transport $^{14}C$-labelled alpha-methyl-glucopyranoside ($^{14}C$-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 μg/ml zeocin (Invitrogen), and HEK293-hSGLT2 cells are cultivated in DMEM medium with 10% foetal calf serum and 250 μg/ml zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 μl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 μg/ml of gentamycin). 250 μl of assay buffer and 5 μl of test compound are then added to each well and the plate is incubated for a further 15 minutes in the incubator. 5 μl of 10% DMSO are used as the negative control. The reaction is started by adding 5 μl of $^{14}C$-AMG (0.05 μCi) to each well. After 2 hours' incubation at 37° C., 5% $CO_2$, the cells are washed again with 250 μl of PBS (20° C.) and then lysed by the addition of 25 μl of 0.1 N NaOH (5 min. at 37° C.). 200 μl of MicroScint20 (Packard) are added to each well and incubation is continued for a further 20 min at 37° C. After this incubation the radioactivity of the $^{14}C$-AMG absorbed is measured in a Topcount (Packard) using a $^{14}C$ scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

The compounds of general formula I according to the invention may for example have EC50 values below 1000 nM, particularly below 50 nM.

In view of their ability to inhibit the SGLT activity, the compounds of general formula I according to the invention and the corresponding pharmaceutically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as metformin, sulphonylureas (e.g. glibenclamid, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrat, fenofibrat), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramin or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully $\frac{1}{5}$ of the lowest dose normally recommended up to $\frac{1}{1}$ of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

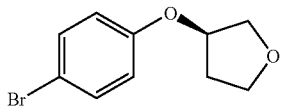

4-((R)-Tetrahydrofuran-3-yloxy)-bromobenzene

Prepared by stirring 10 g of 4-bromophenol with 21 g of ((S)-tetrahydrofuran-3-yl) p-toluenesulphonate in the presence of 11.98 g of potassium carbonate in 100 ml of dimethylformamide at 60° C. for 32 hours and subsequently purifying by chromatographic purification.

Yield: 13.7 g (97% of theory)

Rf value: 0.80 (aluminium oxide; cyclohexane/ethyl acetate=2:1)

The following compound is prepared analogously to Example I:

(1) 4-((S)-tetrahydrofuran-3-yloxy)-bromobenzene

Mass spectrum: m/z=242/244 [M$^+$]

EXAMPLE II

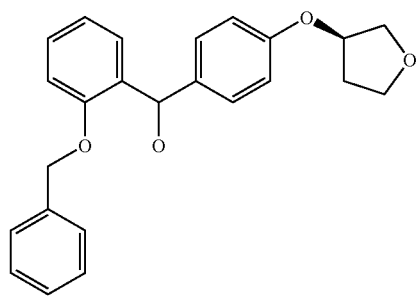

(2-Benzyloxy-phenyl)-[4-((R)-tetrahydrofuran-3-yloxy)phenyl]-methanol 5.17 ml of a 1.6 M butyllithium solution in hexane are added dropwise to a solution of 2.0 g of 4-((R)-tetrahydrofuran-3-yloxy)-bromobenzene in 10 ml of tetrahydrofuran at −78° C. and stirred for another hour at −78° C. Then 1.75 g of 2-benzyloxy-benzaldehyde dissolved in 5 ml of tetrahydrofuran are added dropwise and the mixture is stirred for 2 hours at −78° C. After heating to ambient temperature it is stirred for 1 hour. After aqueous working up and extraction with ethyl acetate the organic phase is dried and evaporated down. The residue is purified by chromatography through a silica gel column with cyclohexane/ethyl acetate (8:2 to 1:1).

Yield: 2.6 g (84% of theory)

$R_f$ value: 0.25 (silica gel, cyclohexane/ethyl acetate=3:1)

The following compounds are prepared analogously to Example II:

(1) (2-benzyloxy-phenyl)-[4-((S)-tetrahydrofuran-3-yloxy)phenyl]-methanol

Mass spectrum (ESI$^+$): m/z=394 [M+NH$_4$]$^+$ (2) (2-benzyloxy-4-fluoro-phenyl)-[4-((R)-tetrahydrofuran-3-yloxy)phenyl]-methanol Mass spectrum (ESI$^+$): m/z=417 [M+Na]$^+$ (3) (2-benzyloxy-6-methoxy-phenyl)-[4-((R)-tetrahydrofuran-3-yloxy)phenyl]-methanol Mass spectrum (ESI$^+$): m/z=424 [M+NH$_4$]$^+$

EXAMPLE III

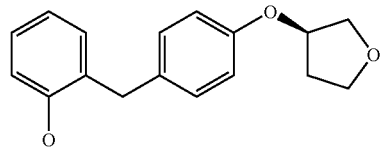

2-[4-((R)-Tetrahydrofuran-3-yloxy)benzyl]-phenol

Prepared from 1.97 g of the compound of Example II by catalytic hydrogenation in methanol in the presence of 0.4 g palladium on activated charcoal (10% Pd) at ambient temperature.

$R_f$ value: 0.52 (silica gel, cyclohexane/ethyl acetate=2:1)

Mass spectrum (ESI$^-$): m/z=269 [M−H]$^-$

The following compounds are prepared analogously to Example III:

(1) 2-[4-((S)-tetrahydrofuran-3-yloxy)benzyl]-phenol

Mass spectrum (ESI$^+$): m/z=271 [M+H]$^+$ (2) 2-[4-((R)-tetrahydrofuran-3-yloxy)benzyl]-4-fluorophenol Mass spectrum (ESI$^-$): m/z=287 [M−H]$^-$ (3) 2-[4-((R)-tetrahydrofuran-3-yloxy)benzyl]-6-methoxyphenol Mass spectrum (ESI$^+$): m/z=301 [M+H]$^+$

EXAMPLE IV

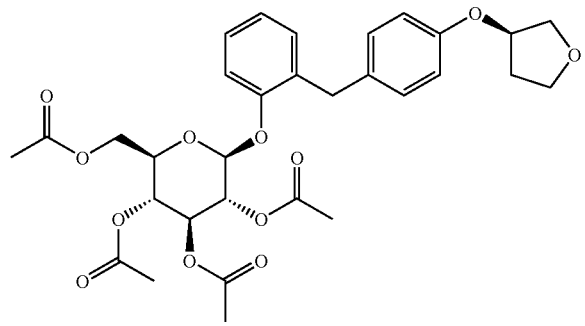

1-(2,3,4,6-Tetra-O-acetyl-β-D-glucopyranosyloxy)-
2-[4-((R)-tetrahydrofuran-3-yloxy)benzyl]-benzene 500 mg of 2-[4-((R)-tetrahydrofuran-3-yloxy)benzyl]-phenol, 820 mg of 2,3,4,6-tetra-O-acetyl-alpha-glucopyranosylbromide, 2 ml of 1M sodium hydroxide solution and 5 ml of chloroform are stirred for 16 hours at ambient temperature. Another 400 mg of 2,3,4,6-tetra-O-acetyl-alpha-glucopyranosylbromide, 1 ml of 1M sodium hydroxide solution and 5 ml of methylene chloride are added and the mixture is stirred for 2.5 days. The organic phase is separated off, washed with water, dried and evaporated down. The crude product is purified by chromatography through a silica gel column with a cyclohexane/ethyl acetate gradient (7:3 to 1:1).

Yield: 440 mg (40% of theory)
Rf value: 0.10 (silica gel; cyclohexane/ethyl acetate=2:1)
Mass spectrum (ESI$^+$): m/z=618 [M+NH$_4$]$^+$ The following compounds are obtained analogously to Example IV:

(1) 1-(2,3,4,6-Tetra-O-acetyl-β-D-glucopyranosyloxy)-2-(4-ethynylbenzyl)-benzene

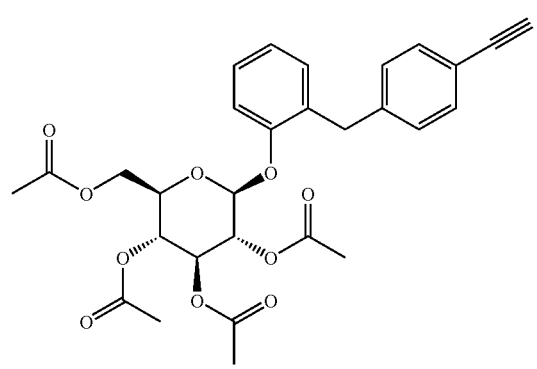

reacting with the compound of Example VI in the presence of benzyl-triethylammonium-bromide Rf value: 0.30 (silica gel; cyclohexane/ethyl acetate=2:1)
Mass spectrum (ESI$^+$): m/z=556 [M+NH$_4$]$^+$ (2) 1-(2,3,4,6-Tetra-O-acetyl-β-D-glucopyranosyloxy)-2-[4-((S)-tetrahydrofuran-3-yloxy)benzyl]-benzene
Rf value: 0.50 (silica gel; cyclohexane/ethyl acetate=1:1)
Mass spectrum (ESI$^+$): m/z=618 [M+NH$_4$]$^+$ (3) 1-(2,3,4,6-Tetra-O-acetyl-β-D-glucopyranosyloxy)-2-[4-((R)-tetrahydrofuran-3-yloxy)benzyl]-4-fluoro-benzene
Mass spectrum (ESI$^+$): m/z=636 [M+NH$_4$]$^+$ (4) 1-(2,3,4,6-Tetra-O-acetyl-β-D-glucopyranosyloxy)-2-[4-((R)-tetrahydrofuran-3-yloxy)benzyl]-6-methoxy-benzene
Mass spectrum (ESI$^+$): m/z=648 [M+NH$_4$]$^+$

EXAMPLE V

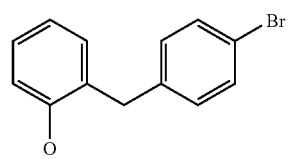

2-(4-Bromobenzyl)-phenol

Prepared by reacting sodium phenoxide (from 4.0 g phenol and 1.7 g 60% sodium hydride in paraffin oil) with 10.27 g of 4-bromobenzyl chloride in toluene at reflux temperature and purifying the reaction mixture by chromatography through a silica gel column with cyclohexane/ethyl acetate (8:2 to 1:1).

Yield: 1.8 g (16% of theory)
Rf value: 0.40 (silica gel; cyclohexane/ethyl acetate=4:1)
Mass spectrum (ESI$^-$): m/z=261/263 [M−H]$^-$

EXAMPLE VI

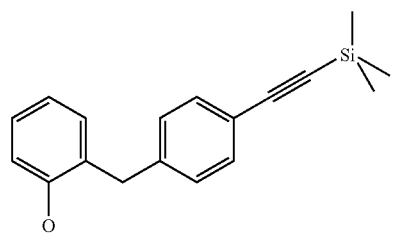

2-[4-(2-Trimethylsilyl-ethynyl)-benzyl]-phenol

Prepared by reacting 1.6 g 2-(4-bromobenzyl)-phenol with 1.03 ml trimethylsilyl-acetylene in the presence of 86 mg of bis(triphenylphosphine)-palladium(II)-chloride and 23 mg of copper (I) iodide in 5 ml of triethylamine at 100° C. in the microwave oven and purifying the reaction mixture by chromatography through a silica gel column with cyclohexane/ethyl acetate (9:1 to 7:3)

Rf value: 0.62 (silica gel; cyclohexane/ethyl acetate=4:1)
Mass spectrum (ESI$^+$): m/z=281 [M+H]$^+$ Preparation of the Final Compounds:

EXAMPLE 1

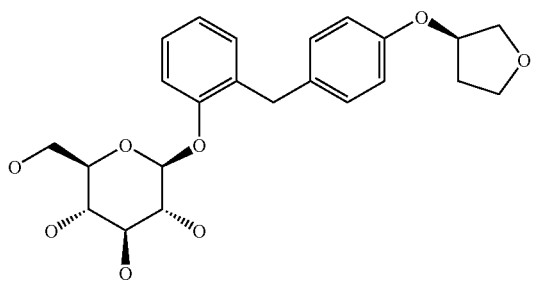

1-(β-D-Glucopyranosyloxy)-2-[4-((R)-tetrahydrofuran-3-yloxy)benzyl]-benzene

A solution of 400 mg of 1-(2,3,4,6-tetra-O-acetyl-β-D-glucopyranosyloxy)-2-[4-((R)-tetrahydrofuran-3-yloxy)benzyl]-benzene in a mixture of 2.5 ml of methanol and 5 ml of tetrahydrofuran is cooled in the ice bath and combined with 3.02 ml of a 1M aqueous lithium hydroxide solution and stirred for 1 hour. The reaction mixture is combined with 5 ml of water and extracted with ethyl acetate. The organic phase is separated off, washed with saturated saline solution, dried and evaporated down.

Yield: 190 mg (65% of theory)

Rf value: 0.23 (silica gel; methylene chloride/methanol=9:1)

Mass spectrum (ESI$^+$): m/z=433 [M+H]$^+$

The following compounds are obtained analogously to Example 1:

(1) 1-(β-D-glucopyranosyloxy)-2-(4-ethynylbenzyl)-benzene

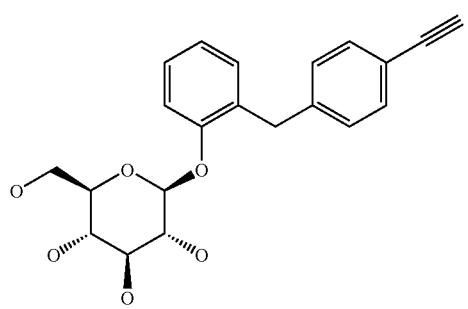

R$_f$ value: 0.55 (silica gel, methylene chloride/methanol=6:1)

Mass spectrum (ESI$^+$): m/z=388 [M+NH$_4$]$^+$ (2) 1-(β-D-glucopyranosyloxy)-2-[4-((S)-tetrahydrofuran-3-yloxy)benzyl]-benzene

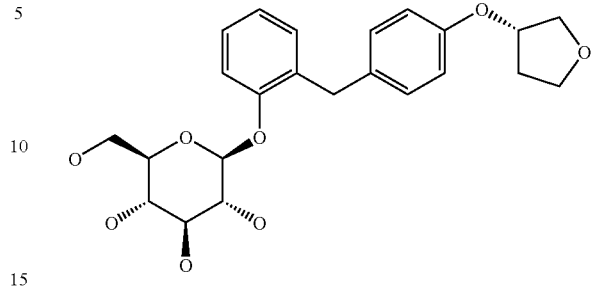

melting point: 134-135° C.

(3) 1-(β-D-glucopyranosyloxy)-2-[4-((R)-tetrahydrofuran-3-yloxy)benzyl]-4-fluoro-benzene

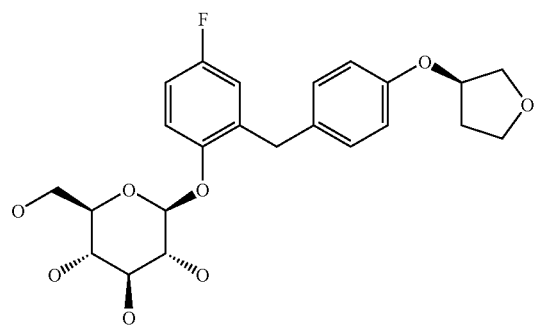

melting point: 145-147° C.

(4) 1-(β-D-glucopyranosyloxy)-2-[4-((R)-tetrahydrofuran-3-yloxy)benzyl]-6-methoxy-benzene

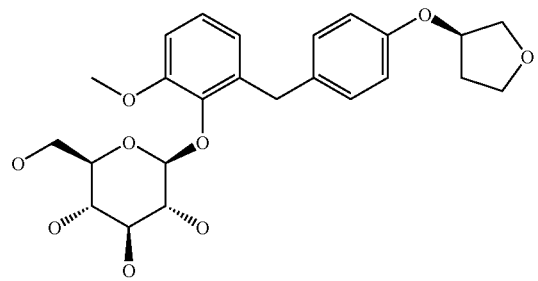

Mass spectrum (ESI$^+$): m/z=480 [M+NH$_4$]$^+$

EXAMPLE 2

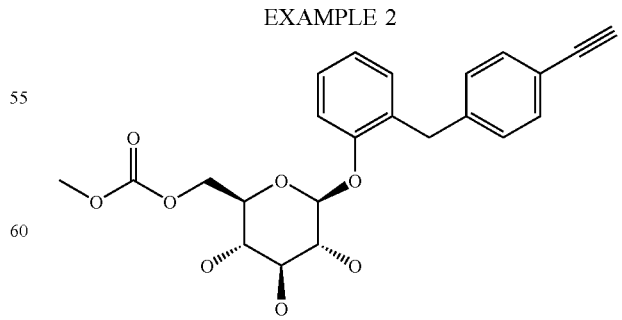

1-(6-O-Methoxycarbonyl-β-D-glucopyranosyloxy)-2-(4-ethynylbenzyl)-benzene 100 mg of 1-(β-D-glucopyranosyloxy)-2-(4-ethynylbenzyl)-benzene in 0.5 ml of 2,4,6-collidine are combined with 0.026 ml of methyl chloroformate in the ice bath and then stirred for 16 hours at ambient temperature. 5 ml of 0.1 N hydrochloric acid are added to the reaction mixture which is then extracted with 10 ml of ethyl acetate. The organic phase is separated off, washed with saturated saline solution and evaporated down. The residue is stirred with 8 ml of diethyl ether/petroleum ether (1:1), the solid is suction filtered and dried at 40° C.

Yield: 73.5 mg (63% of theory)

Mass spectrum (ESI$^+$): m/z=429 [M+H]$^+$

The following compounds are obtained analogously to Example 2:

(1)  1-(6-O-methoxycarbonyl-β-D-glucopyranosyloxy)-2-[4-((R)-tetrahydrofuran-3-yloxy)benzyl]-benzene

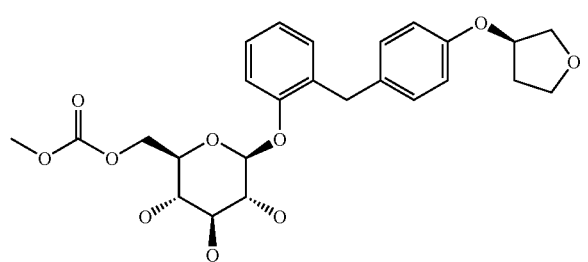

Mass spectrum (ESI$^+$): m/z=508 [M+NH$_4$]$^+$ (2)  1-(6-O-methoxycarbonyl-β-D-glucopyranosyloxy)-2-[4-((S)-tetrahydrofuran-3-yloxy)benzyl]-benzene

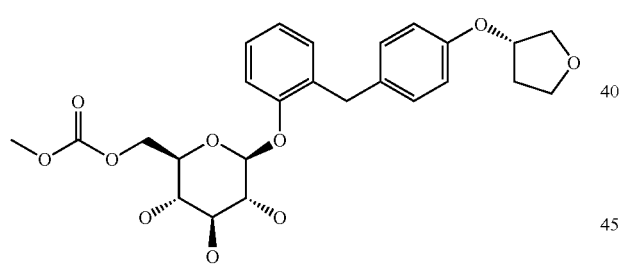

melting point: 149-150° C.

The following compounds are also prepared analogously to the above-mentioned Examples and other methods known from the literature:

(10)
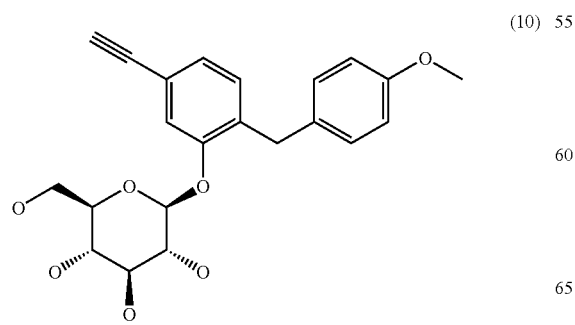

-continued

(11)
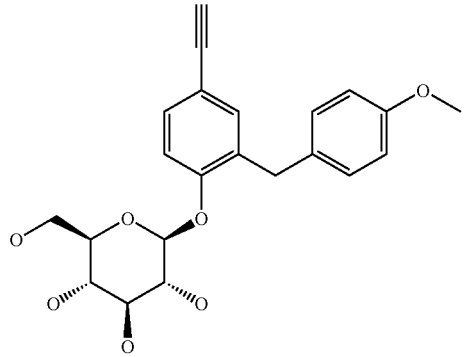

(12)
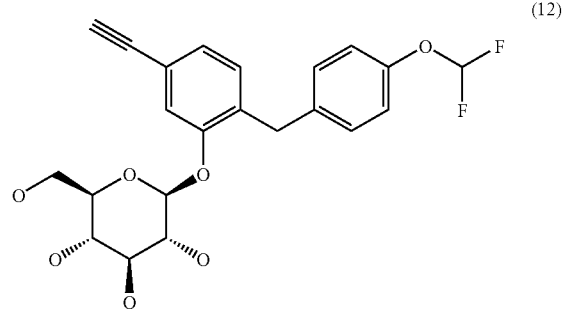

(13)
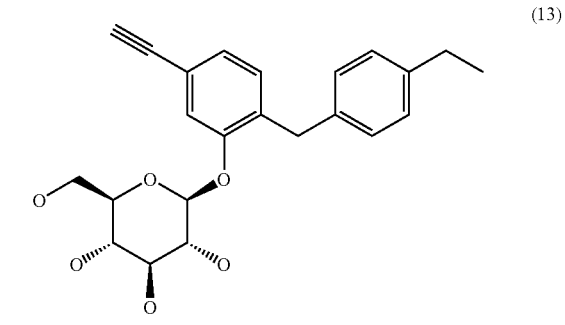

(14)
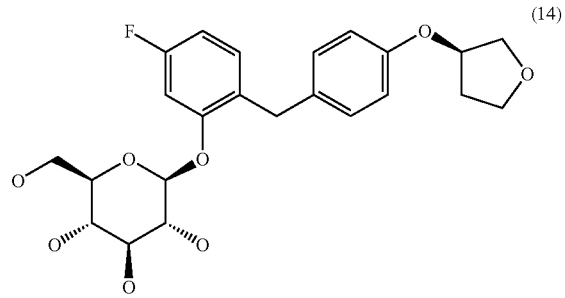

(15)
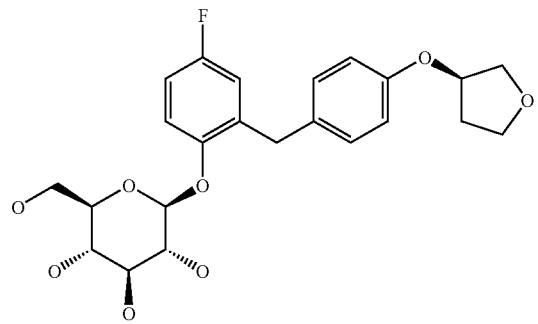

(16)
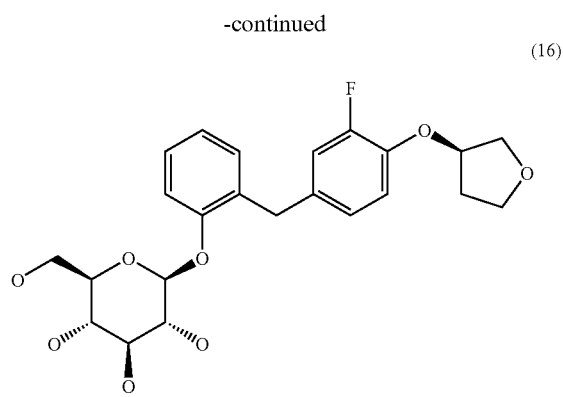
(17)
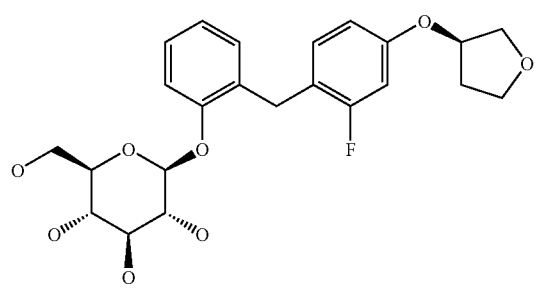
(18)
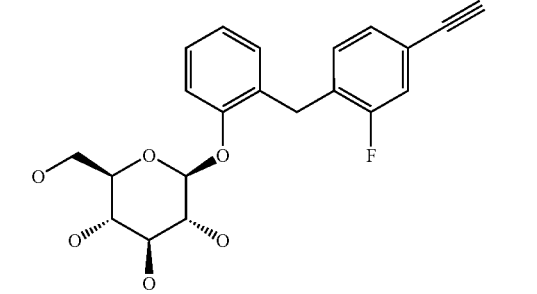
(19)
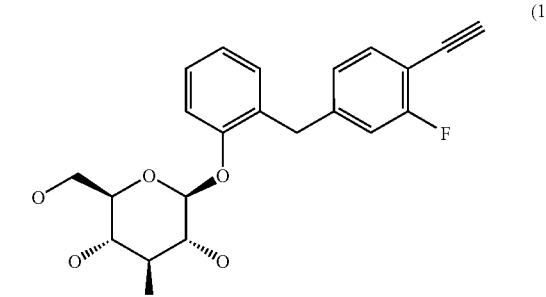
(20)
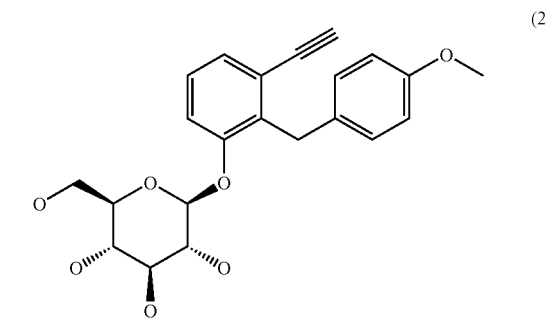
(21)
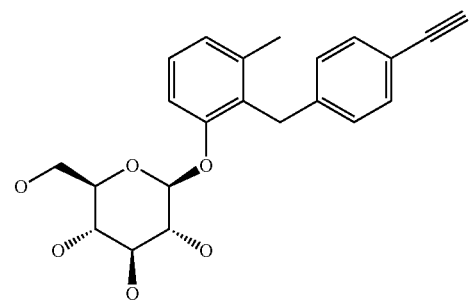
(22)
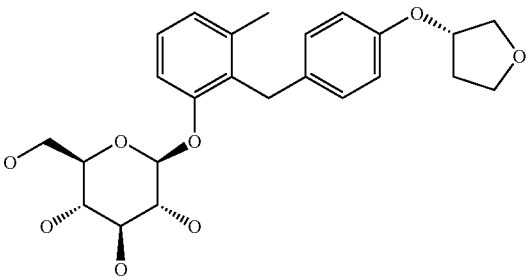
(23)
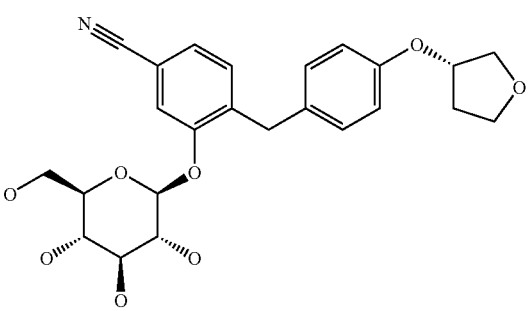
(24)
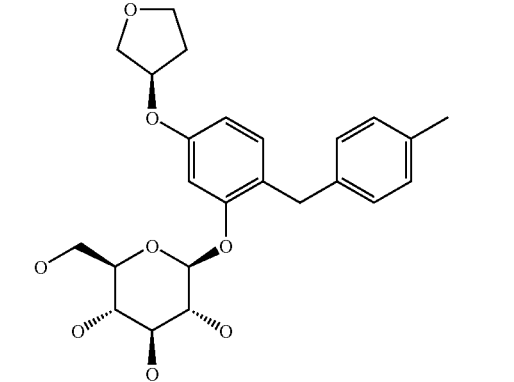
(25)
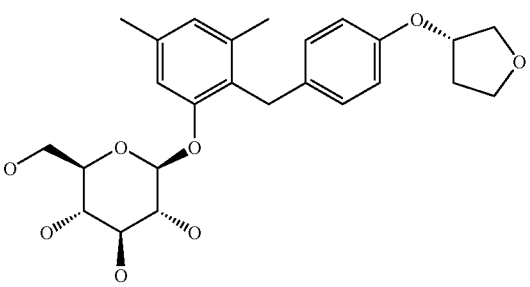

-continued

(26)
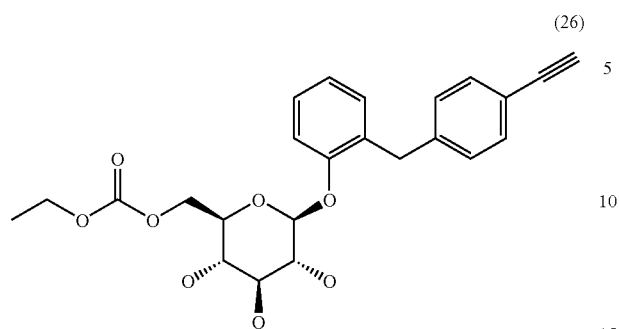

(27)
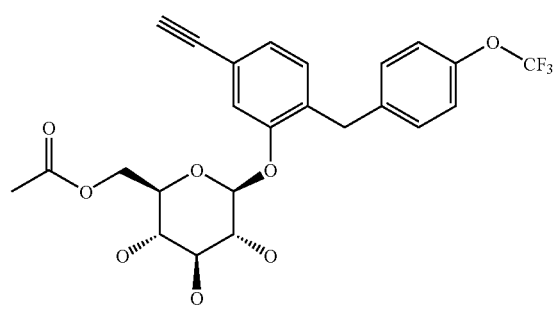

(28)
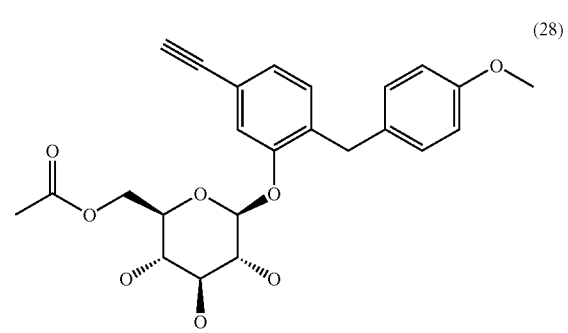

(29)
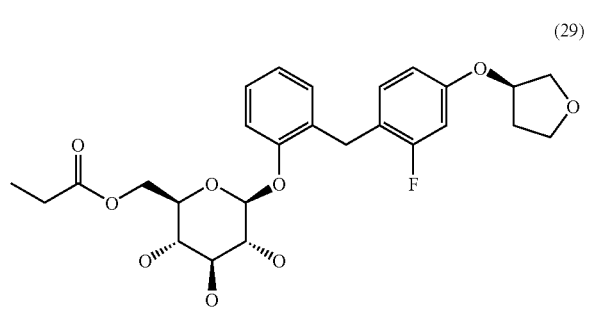

-continued

(30)
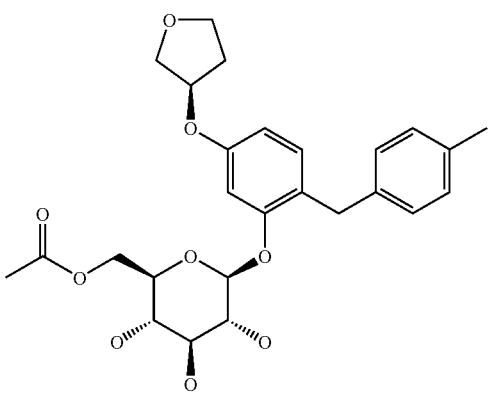

EXAMPLE A

Tablets Containing 100 mg of Active Substance

| Composition: | |
|---|---|
| 1 tablet contains: | |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE B

Tablets Containing 150 mg of Active Substance

| Composition: | |
|---|---|
| 1 tablet contains: | |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| die: | 10 mm, flat |

EXAMPLE C

Hard Gelatine Capsules Containing 150 mg of Active Substance

| Composition: | | |
|---|---|---|
| 1 capsule contains: | | |
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| | |
|---|---|
| Capsule filling: | approx. 320 mg |
| Capsule shell: | size 1 hard gelatine capsule. |

EXAMPLE D

Suppositories Containing 150 mg of Active Substance

| Composition: | |
|---|---|
| 1 suppository contains: | |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

Ampoules Containing 10 mg Active Substance

| Composition: | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE F

Ampoules Containing 50 mg of Active Substance

| Composition: | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:

1. A glucopyranozyloxy-substituted aromatic compound formula (I):

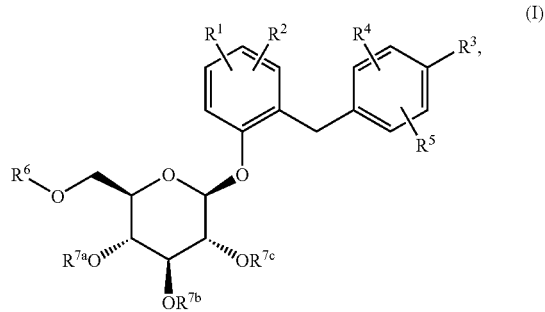

wherein
  $R^1$ is $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy or tetrahydropyranyl-$C_{1-3}$-alkyloxy, or,
    if $R^3$ is selected from the group consisting of $C_{2-6}$-alkylnyl, tetrahydrofuran-3-yloxy, tetrahydropyran-3-yloxy, tetrahydropyran-4-yloxy, tetrahydrofuranyl-$C_{1-3}$-alkyloxy and tetrahydropyranyl-$C_{1-3}$-alkyloxy,
    then $R^1$ may additionally be hydrogen, fluorine, chlorine, bromine, iodine, $C_{1-4}$-alkyl, a methyl group substituted by 1 to 3 fluorine atoms, an ethyl group substituted by 1 to 5 fluorine atoms, $C_{1-4}$-alkoxy, a methoxy group substituted by 1 to 3 fluorine atoms, an ethoxy group substituted by 1 to 5 fluorine atoms, a $C_{1-4}$-alkyl group substituted by a hydroxy or $C_{1-3}$-alkoxy group, a $C_{2-4}$-alkoxy group substituted by a hydroxy or $C_{1-3}$-alkoxy group, $C_{2-6}$-alkenyl, $C_{3-6}$-cycloalkyl, $C_{3-6}$-cycloalkyl-$C_{1-3}$-alkyl, $C_{3-6}$-cycloalkoxy, $C_{3-6}$-cycloalkyl-$C_{1-3}$-alkoxy, hydroxy, amino or cyano, $R^2$ is hydrogen, fluorine, chlorine, methyl, methyl or methoxy substituted by 1 to 3 fluorine atoms, $R^3$ is $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy or tetrahydropyranyl-$C_{1-3}$-alkyloxy, or, if $R^1$ is selected from the group consisting of $C_{2-6}$-alkynyl, tetrahydrofuran-3-yloxy, tetrahydropyran-3-yloxy, tetrahydropyran-4-yloxy, tetrahydrofuranyl-$C_{1-3}$-alkyloxy and tetrahydropyranyl-$C_{1-3}$-alkyloxy, then $R^3$ may additionally be hydrogen, fluorine, chlorine, bromine, iodine, $C_{1-6}$-alkyl, $C_{2-6}$-alkenyl, $C_{3-6}$-cycloalkyl, $C_{3-6}$-cycloalkylidenemethyl, $C_{1-6}$-alkoxy, $C_{3-6}$-cycloalkyl-oxy, $C_{3-6}$-cycloalkyl-$C_{1-3}$-alkoxy, aryl, aryl-$C_{1-3}$-alkyl, heteroaryl, heteroaryl-$C_{1-3}$-alkyl, aryloxy, aryl-$C_{1-3}$-alkyl-oxy, a methyl or methoxy group substituted by 1 to 3 fluorine atoms, a $C_{2-4}$-alkyl or $C_{2-4}$-alkoxy group substituted by 1 to 5 fluorine atoms, a $C_{1-4}$-alkyl group substituted by a cyano group, a $C_{1-4}$-alkyl group substituted by a hydroxy or $C_{1-3}$-alkyloxy group, cyano, carboxy, $C_{1-3}$-alkoxycarbonyl, aminocarbonyl, ($C_{1-3}$-alkylamino)carbonyl, di-($C_{1-3}$-alkyl)aminocarbonyl, pyrrolidin-1-ylcarbonyl, piperidin-1-ylcarbonyl, morpholin-4-ylcarbonyl, piperazin-1-yl-carbonyl, 4-($C_{1-3}$-alkyl)-piperazin-1-ylcarbonyl, nitro, amino, $C_{1-3}$-alkylamino, di-($C_{1-3}$-alkyl)amino, ($C_{1-4}$-alkyl)carbonylamino, $C_{1-4}$-alkylsulphonylamino, arylsulphonylamino, aryl-$C_{1-4}$alkylsulphonylamino, $C_{1-4}$-alkylsulphanyl, $C_{1-4}$-alkylsulphinyl, $C_{1-4}$-alkylsulphonyl, arylsulphenyl, arylsulphinyl or arylsulphonyl, $R^4$ and $R^5$, which may be identical or different, are hydrogen, fluorine, chlorine, bromine, $C_{1-3}$-alkyl, $C_{1-3}$-alkoxy, methyl or methoxy substituted by 1 to 3 fluorine atoms, and $R^{6a}$, $R^{7a}$, $R^{7b}$, $R^{7c}$ independently of one another are hydrogen, ($C_{1-18}$-alkyl)carbonyl, ($C_{1-18}$-alkyl)oxycarbonyl, arylcarbonyl or aryl-($C_{1-3}$-alkyl)-carbonyl, while the aryl groups mentioned in the definition of the above groups are phenyl or naphthyl groups which may be mono- or disubstituted independently of one another by $R_h$, while the substituents may be identical or different and $R_h$ is fluorine, chlorine, bromine, iodine, $C_{1-3}$-alkyl, difluoromethyl, trifluoromethyl, $C_{1-3}$-alkoxy, difluoromethoxy, trifluoromethoxy or cyano, the heteroaryl groups mentioned in the definition of the above-mentioned groups are a pyrrolyl, furanyl, thienyl, imidazolyl, pyridyl, indolyl, benzofuranyl, benzothiophenyl, quinolinyl or isoquinolinyl group, or a pyrrolyl, furanyl, thienyl, imidazolyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted by $R_h$, while the substituents may be identical or different and $R_h$ is as hereinbefore defined, while, unless otherwise stated, the above-mentioned alkyl groups may be straight-chain or branched, or a tautomer or stereoisomer thereof or mixtures thereof or a salt thereof.

2. A glucopyranosyloxy-substituted aromatic compound of formula I according to claim 1, wherein $R^1$ is ethynyl, or, if $R^3$ is selected from the group consisting of ethynyl, tetrahydrofuran-3-yloxy, tetrahydropyran-3-yloxy, tetrahydropyran-4-yloxy, tetrahydrofuranyl methyloxy and tetrahydropyranylmethyloxy, then $R^1$ may additionally be hydrogen, fluorine, chlorine, methyl, difluoromethyl, trifluoromethyl, methoxy, difluoromethoxy, trifluoromethoxy or cyano, $R^2$ is hydrogen, fluorine or methyl, $R^3$ is ethynyl, tetrahydrofuran-3-yloxy, tetrahydropyran-3-yloxy, tetrahydropyran-4-yloxy, tetrahydrofuranylmethyloxy or tetrahydropyranylmethyloxy, or, if $R^1$ is ethynyl, then $R^3$ may additionally be hydrogen, fluorine, chlorine, methyl, ethyl, isopropyl, tert-butyl, 2-cyano-2-propyl, difluoromethyl, trifluoromethyl, cyclopropyl, cyclobutyl, cyclopentyl, methoxy, ethoxy, isopropoxy, difluoromethoxy, trifluoromethoxy, 1,1,2,2-tetrafluoroethoxy, cylopropyloxy, cyclobutyloxy, cyclopentyloxy, methylsulphanyl, 2-methyl-1-propen-1-yl, cyclopropylidenemethyl, phenyl, fluorophenyl, pyridinyl, pyrimidinyl, pyridazinyl, pyrazinyl, imidazolyl, pyrazolyl, triazolyl, tetrazolyl, oxazolyl, oxadiazolyl, thiazolyl or thiadiazolyl, $R^4$ is hydrogen, fluorine or methyl, $R^5$ is hydrogen, $R^6$, $R^{7a}$, $R^{7b}$, $R^{7c}$ independently of one another are hydrogen, ($C_{1-18}$-alkyl)carbonyl, ($C_{1-18}$-alkyl)oxycarbonyl, arylcarbonyl or aryl-($C_{1-3}$-alkyl)-carbonyl, or a tautomer or stereoisomer thereof or mixtures thereof or a salt thereof.

3. A glucopyranosyloxy-substituted aromatic compound of formula I according to claim 1, wherein $R^1$ is ethynyl or, if $R^3$ is selected from the group consisting of ethynyl and tetrahydrofuran-3-yloxy, then $R^1$ may additionally be hydrogen, fluorine, methyl, methoxy or cyano, $R^2$ is hydrogen or methyl, $R^3$ is ethynyl or tetrahydrofuran-3-yloxy or, if $R^1$ is ethynyl, then $R^3$ may additionally be methyl, ethyl, methoxy, difluoromethoxy or trifluoromethoxy, $R^4$ is hydrogen or fluorine, $R^5$ is hydrogen, $R^6$, $R^{7a}$, $R^{7b}$, $R^{7c}$ independently of one another are hydrogen, ($C_{1-18}$-alkyl)carbonyl, ($C_{1-18}$-alkyl)oxycarbonyl, arylcarbonyl or aryl-($C_{1-3}$-alkyl)-carbonyl, or a tautomer or stereoisomer thereof or mixtures thereof or a salt thereof.

4. A glucopyranosyloxy-substituted aromatic compound of formula I according to claim 1 selected from the group consisting of (a) 1-(β-D-glucopyranosyloxy)-2-[4-((R)-tetrahydrofuran-3-yloxy)benzyl]-benzene, and (b) 1-(β-D-glucopyranosyloxy)-2-(4-ethynylbenzyl)-benzene, or a derivative thereof wherein $R^6$ has a meaning according to claim 1 other than hydrogen,
or a tautomer or stereoisomer thereof or mixtures thereof or a salt thereof.

5. A physiologically acceptable salt of a compound according to claim 1 with an inorganic or organic acid.

6. A pharmaceutical composition comprising a salt of a compound of claim 5 and one or more inert carriers and/or diluents.

7. A physiologically acceptable salt of a compound according to claim 2 with an inorganic or organic acid.

8. A pharmaceutical composition comprising a salt of a compound of claim 7 and one or more inert carriers and/or diluents.

9. A physiologically acceptable salt of a compound according to claim 3 with an inorganic or organic acid.

10. A pharmaceutical composition comprising a salt of a compound of claim 9 with and one or more inert carriers and/or diluents.

11. A physiologically acceptable salt of a compound according to claim 4 with an inorganic or organic acids acid.

12. A pharmaceutical composition comprising salt of a compound of claim 11 and one or more inert carriers and/or diluents.

13. A method of treatment of a metabolic disorder selected from the group consisting of type 1 and type 2 diabetes mellitus, and complications of diabetes, comprising administering a therapeutically effective amount of a compound according to claim 1 or a physiologically acceptable salt thereof to a patient in need thereof.

14. A method of treatment of a metabolic disorder selected from the group consisting of type 1 and type 2 diabetes mellitus, and complications of diabetes, comprising administering a therapeutically effective amount of a compound according to claim 2 or a physiologically acceptable salt thereof to a patient in need thereof.

15. A method of treatment of a metabolic disorder selected from the group consisting of type 1 and type 2 diabetes mellitus, and complications of diabetes, comprising administering a therapeutically effective amount of a compound according to claim 3 or a physiologically acceptable salt thereof to a patient in need thereof.

16. A method of treatment of a metabolic disorder selected from the group consisting of type 1 and type 2 diabetes mellitus, and complications of diabetes, comprising administering a therapeutically effective amount of a compound according to claim 4 or a physiologically acceptable salt thereof to a patient in need thereof.

17. A method of reducing the degeneration of pancreatic beta cells and/or for improving and/or restoring the functionality of pancreatic beta cells comprising administering to a patient in need thereof a pharmaceutically effective amount of a compound according to claim 1 or a physiologically acceptable salt thereof.

18. A method of reducing the degeneration of pancreatic beta cells and/or for improving and/or restoring the functionality of pancreatic beta cells comprising administering to a patient in need thereof a pharmaceutically effective amount of a compound according to claim 2 or a physiologically acceptable salt thereof.

19. A method of reducing the degeneration of pancreatic beta cells and/or for improving and/or restoring the functionality of pancreatic beta cells comprising administering to a patient in need thereof a pharmaceutically effective amount of a compound according to claim 3 or a physiologically acceptable salt thereof.

20. A method of reducing the degeneration of pancreatic beta cells and/or for improving and/or restoring the functionality of pancreatic beta cells comprising administering to a patient in need thereof a pharmaceutically effective amount of a compound according to claim 4 or a physiologically acceptable salt thereof.

21. A method of treating hypertensiveness and/or diuretic conditions comprising administering to a patient in need thereof a therapeutically effective amount of a compound according to claim 1 or a physiologically acceptable salt thereof.

22. A process for preparing a pharmaceutical composition comprising incorporating a compound according to formula I of claim 1 or a physiologically acceptable salt thereof into one or more inert carriers and/or diluents by a non-chemical method.

23. A process for preparing a pharmaceutical composition comprising incorporating a compound according to claim 2 or a physiologically acceptable salt thereof into one or more inert carriers and/or diluents by a non-chemical method.

24. A process for preparing a pharmaceutical composition comprised of the step of comprising incorporating a compound according to claim 3 or a physiologically acceptable salt thereof into one or more inert carriers and/or diluents by a non-chemical method.

25. A process for preparing a pharmaceutical composition comprising incorporating a compound according to claim 4 or a physiologically acceptable salt thereof into one or more inert carriers and/or diluents by a non-chemical method.

26. A process for preparing a compound of formula I according to claim 1, wherein $R^6$, $R^{7a}$, $R^{7b}$ and $R^{7c}$ are defined as in claim 1, but do not represent hydrogen, comprising reacting a a compound of formula (II):

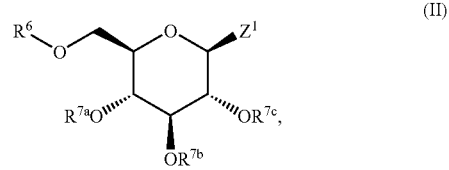

wherein
$R^6$ and $R^{7a}$, $R^{7b}$, $R^{7c}$ are as hereinbefore defined, but do not represent hydrogen, and $Z^1$ is a leaving group, with a compound of formula (III):

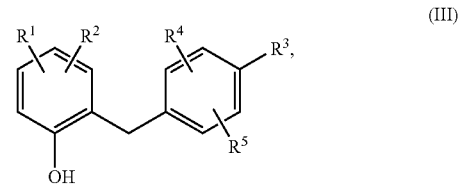

wherein
$R^1$ to $R^5$ are defined as in claim 1.

27. A process for preparing a compound of formula I according to claim 1 wherein $R^6$, $R^{7a}$, $R^{7b}$ and $R^{7c}$ represent hydrogen comprising hydrolyzing a compound of formula I wherein $R^6$ and $R^{7a}$, $R^{7b}$, $R^{7c}$ are as hereinbefore defined, but do not represent hydrogen, and optionally, converting a compound of formula I thus obtained wherein $R^6$ is a hydrogen atom by acylation into a corresponding acyl compound of formula I, and/or optionally, cleaving any protecting group used during the reactions and optionally, resolving the compound of formula I thus obtained into a stereoisomer thereof and/or optionally, converting the compound of formula I into a salt thereof.

28. A compound of claim 4, wherein $R^6$ is ethoxycarbonyl or methoxycarbonyl.

* * * * *